United States Patent
Nagar et al.

(10) Patent No.: US 11,852,899 B2
(45) Date of Patent: Dec. 26, 2023

(54) ULTRASOUND EMITTING CONTACT LENS

(71) Applicant: International Business Machines Corporation, Armonk, NY (US)

(72) Inventors: Raghuveer Prasad Nagar, Kota (IN); Sarbajit K. Rakshit, Kolkata (IN); Reji Jose, Bangalore (IN); Sidharth Ullal, Chennai (IN)

(73) Assignee: International Business Machines Corporation, Armonk, NY (US)

( * ) Notice: Subject to any disclaimer, the term of this patent is extended or adjusted under 35 U.S.C. 154(b) by 304 days.

(21) Appl. No.: 17/064,474

(22) Filed: Oct. 6, 2020

(65) Prior Publication Data
US 2022/0107514 A1   Apr. 7, 2022

(51) Int. Cl.
| | | |
|---|---|---|
| G02C 11/00 | (2006.01) | |
| A61L 12/02 | (2006.01) | |
| B06B 1/06 | (2006.01) | |
| G02C 7/04 | (2006.01) | |

(52) U.S. Cl.
CPC ............ *G02C 11/10* (2013.01); *A61L 12/026* (2013.01); *B06B 1/0622* (2013.01); *G02C 7/04* (2013.01)

(58) Field of Classification Search
CPC ......... G02C 11/10; G02C 7/04; A61L 12/026; B06B 1/0622; B06B 1/0625
See application file for complete search history.

(56) References Cited

U.S. PATENT DOCUMENTS

| | | | |
|---|---|---|---|
| 6,183,705 B1 * | 2/2001 | Chang | G02C 13/008 |
| | | | 422/301 |
| 8,324,595 B2 | 12/2012 | Takahashi | |
| 9,454,003 B1 * | 9/2016 | Li | G02B 7/026 |
| 9,763,827 B2 | 9/2017 | Kelleher | |

(Continued)

FOREIGN PATENT DOCUMENTS

| | | |
|---|---|---|
| EP | 3212137 A1 | 9/2017 |
| KR | 1020130079436 A | 7/2013 |
| WO | 2018039729 A1 | 3/2018 |

OTHER PUBLICATIONS

"Discover Glass Enterprise Edition", Google, Last printed Sep. 12, 2019, 6 pages, <https://www.google.com/glass/start/>.

(Continued)

*Primary Examiner* — Balram T Parbadia
*Assistant Examiner* — Gabriel A Sanz
(74) *Attorney, Agent, or Firm* — Kristofer Haggerty

(57) ABSTRACT

A contact lens for application to a human eyeball capable of emitting ultrasonic pressure waves from a plurality of piezoelectric transducers to mitigate the effects of airborne eye irritants and infectious microorganisms. The piezoelectric transducers converts mechanical energy applied upon the contact lens from the eyelid as the eyelid blinks and/or winks into electrical energy to be used for emitting ultrasonic pressure waves from the piezoelectric transducers. The ultrasonic pressure waves destroy airborne microorganisms near the contact lens. A photodiode onboard the contact lens indicates when the eyelid is not closed in order to limit or prevent emission of ultrasonic pressure waves from the piezoelectric transducers while the eyelid is closed. An antenna onboard the contact lens receives information from augmented reality glasses or other computing devices.

18 Claims, 5 Drawing Sheets

(56) References Cited

U.S. PATENT DOCUMENTS

| | | | | |
|---|---|---|---|---|
| 2011/0084834 | A1* | 4/2011 | Sabeta | G06K 19/077 340/540 |
| 2012/0268712 | A1* | 10/2012 | Egan | G02C 7/04 351/159.34 |
| 2014/0009741 | A1 | 1/2014 | Levien et al. | |
| 2016/0188943 | A1* | 6/2016 | Franz | G06K 7/10831 235/462.2 |
| 2017/0354326 | A1* | 12/2017 | Pugh | A61B 3/10 |
| 2018/0304101 | A1 | 10/2018 | Yang | |
| 2020/0159042 | A1* | 5/2020 | Langford | G02C 7/024 |
| 2020/0159045 | A1* | 5/2020 | Langford | A61B 8/4427 |
| 2020/0333630 | A1* | 10/2020 | Toner | G02C 7/04 |
| 2021/0213913 | A1* | 7/2021 | Hart | G01S 7/497 |

OTHER PUBLICATIONS

Elgan, Mike, "Why a smart contact lens is the ultimate wearable", Computer World, May 9, 2016, 8 pages, <https://www.computerworld.com/article/3066870/why-a-smart-contact-lens-is-the-ultimate-wearable.html>.

Haddrill, Marilyn, "Conjunctivitis: Bacterial, viral, allergic and other types", All About Vision, Page Updated Sep. 2017, 8 pages, <https://www.allaboutvision.com/conditions/conjunctivitis-types.htm>.

Hoover, K., "Ultrasound potentially safe, effective way to kill bacteria", Penn State, Dec. 11, 2012, 2 pages, <https://news.psu.edu/story/187690/2002/12/11/ultrasound-potentially-safe-effective-way-kill-bacteria>.

Maxcy, Kenneth, "The Transmission of Infection Through the Eye", JAMA, Article-Abstract only, Mar. 1, 1919, 72(9), pp. 636-630, <https://jamanetwork.com/journals/jama/article-abstract/220430>.

Schirber, Michael, "New Way to Kill Viruses: Shake Them to Death", Live Science, Feb. 5, 2008, 9 pages, <https://www.livescience.com/7472-kill-viruses-shake-death.html>.

Seedwoodhary et al., "Transmission and Control of Infection in Ophthalmic Practice", Community Eye Health, vol. 12, No. 30, 1999, pp. 25-28.

\* cited by examiner

ULTRASOUND EMITTING CONTACT LENS

BACKGROUND

The present invention relates generally to the field of wearable electronic devices, and more particularly to electronic contact lenses.

Human eyes can become irritated and infected by airborne particles and pathogens. Frequently, worksites that involve manual labor stir up fine particles into the air which may come in contact with unprotected eyes and cause irritations/infections. Typical state of the art protections include hard plastic safety glasses (for example, polycarbonate).

Similar to ultrasonic cleaning, biological cells including bacteria can be disintegrated via ultrasound. High power ultrasound produces cavitation that facilitates particle disintegration or reactions. This has uses in biological science for analytical or chemical purposes (sonication and sonoporation) and in killing bacteria in sewage.

Contact lenses are small hollow spherical domes comprised of translucent material. Typical contact lenses are shaped to provide some degree of vision correction for individuals with impaired vision (such as near-sightedness or far-sightedness).

Ultrasound, or ultrasonic pressure waves, comprises sound waves with frequencies higher than the upper audible limit of human hearing, where sound is a vibration that propagates as an acoustic wave, through a transmission medium such as a gas, solid or liquid. Acoustic waves are a type of energy propagation by means of adiabatic compression and decompression through a medium. An adiabatic compression occurs without transferring heat or mass between a thermodynamic system and its surroundings, which differs from an isothermal process, because an adiabatic process transfers energy to the surroundings only as work.

A photodiode is a semiconductor device that converts light into an electrical current as photons are absorbed in the photodiode.

SUMMARY

According to an aspect of the present invention, there is an ultrasonic emitting electronic contact lens apparatus including: (i) a translucent lens portion having a concave surface and a convex surface; and (ii) a plurality of piezoelectric transducer portions embedded upon the convex surface, where the plurality of piezoelectric transducer portions are arranged along the outer circumference of the convex surface, and the plurality of piezoelectric transducer portions emit ultrasonic pressure waves.

According to an aspect of the present invention, there is a method, computer program product and/or system for use with a contact lens placed on a human eyeball, with the contact lens including a plurality of piezoelectric transducers that performs the following operations (not necessarily in the following order): (i) responsive to a blinking motion of an eyelid over the human eyeball, converting pressure from blinking motion of the eyelid applied to the piezoelectric transducers into electrical energy; and (ii) emitting, using the converted electrical energy, ultrasonic pressure waves through the piezoelectric transducers.

DETAILED DESCRIPTION

Figure 1:
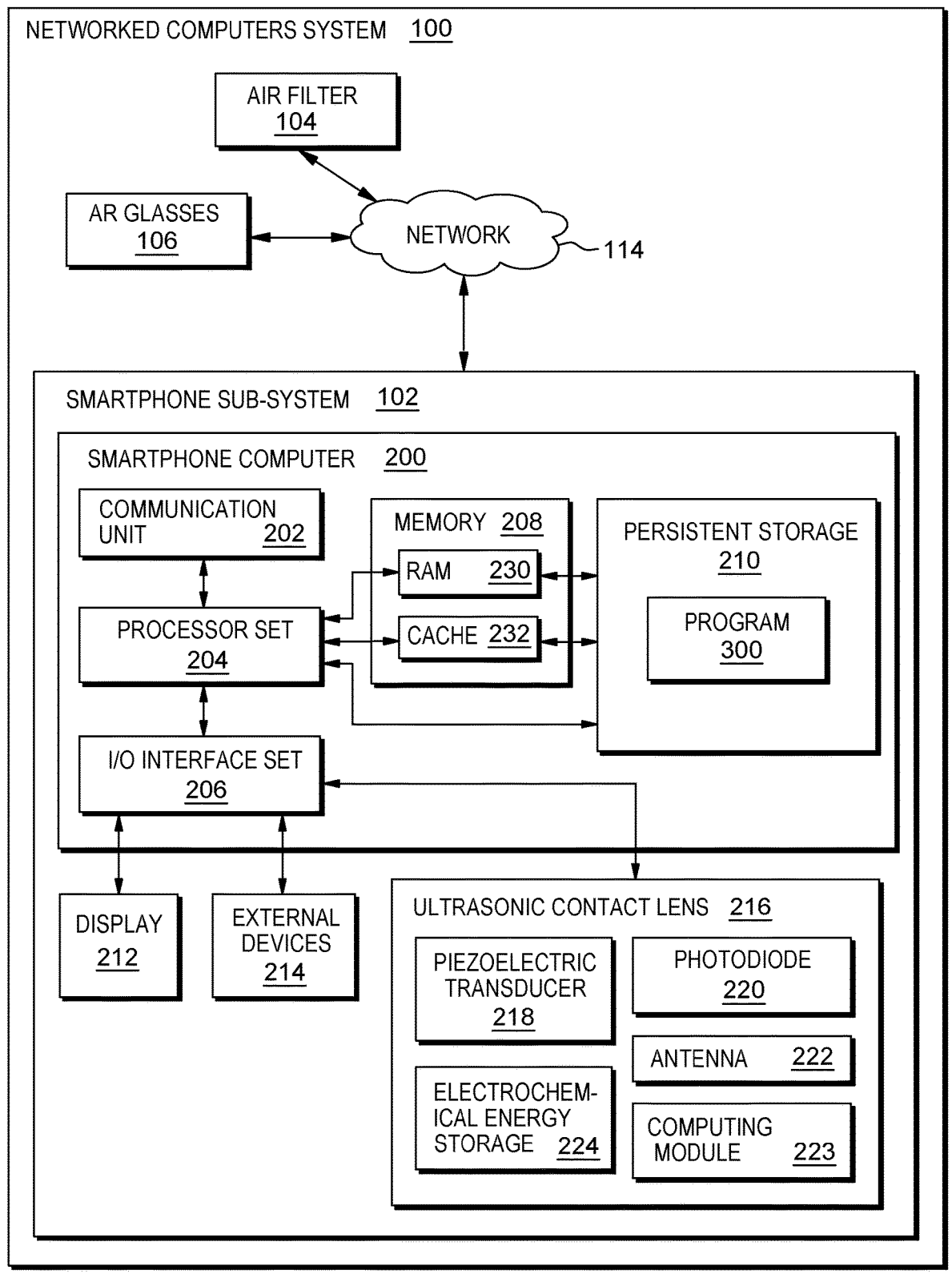
FIG. 1 is a block diagram view of a first embodiment of a system according to the present invention.

Some embodiments of the present invention are directed to a contact lens for application to a human eyeball capable of emitting ultrasonic pressure waves from a plurality of piezoelectric transducers to mitigate the effects of airborne eye irritants and infectious microorganisms. The piezoelectric transducers converts mechanical energy applied upon the contact lens from the eyelid as the eyelid blinks and/or winks into electrical energy to be used for emitting ultrasonic pressure waves from the piezoelectric transducers. The ultrasonic pressure waves destroy airborne microorganisms near the contact lens. A photodiode onboard the contact lens indicates when the eyelid is not closed in order to limit or prevent emission of ultrasonic pressure waves from the piezoelectric transducers while the eyelid is closed. An antenna onboard the contact lens receives information from augmented reality glasses or other computing devices.

This Detailed Description section is divided into the following subsections: (i) The Hardware and Software Environment; (ii) Example Embodiment; (iii) Further Comments and/or Embodiments; and (iv) Definitions.

I. The Hardware and Software Environment

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (for example, light pulses passing through a fiber-optic cable), or electrical signals transmitted through a wire.

A "storage device" is hereby defined to be anything made or adapted to store computer code in a manner so that the computer code can be accessed by a computer processor. A storage device typically includes a storage medium, which is the material in, or on, which the data of the computer code is stored. A single "storage device" may have: (i) multiple discrete portions that are spaced apart, or distributed (for example, a set of six solid state storage devices respectively located in six laptop computers that collectively store a single computer program); and/or (ii) may use multiple storage media (for example, a set of computer code that is partially stored in as magnetic domains in a computer's non-volatile storage and partially stored in a set of semiconductor switches in the computer's volatile memory). The term "storage medium" should be construed to cover situations where multiple different types of storage media are used.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

As shown in FIG. 1, networked computers system 100 is an embodiment of a hardware and software environment for use with various embodiments of the present invention, described in detail with reference to the Figures. Networked computers system 100 includes: ultrasonic eye protection subsystem 102 (sometimes herein referred to, more simply, as subsystem 102); air filter 104; augmented reality (AR) glasses 106; and communication network 114. Ultrasonic eye protection subsystem 102 includes: ultrasonic eye protection computer 200; communication unit 202; processor set 204; input/output (I/O) interface set 206; memory 208; persistent storage 210; display 212; external device(s) 214; ultrasonic contact lens 216; logic unit 217; piezoelectric transducer 218; photodiode 220; antenna 222; computing module 223; random access memory (RAM) 230; cache 232; and program 300.

Subsystem 102 may be a laptop computer, tablet computer, netbook computer, personal computer (PC), a desktop computer, a personal digital assistant (PDA), a smart phone, or any other type of computer (see definition of "computer" in Definitions section, below). Program 300 is a collection of machine readable instructions and/or data that is used to create, manage and control certain software functions that will be discussed in detail, below, in the Example Embodiment subsection of this Detailed Description section.

Subsystem 102 is capable of communicating with other computer subsystems via communication network 114. Network 114 can be, for example, a local area network (LAN), a wide area network (WAN) such as the Internet, or a combination of the two, and can include wired, wireless, or fiber optic connections. In general, network 114 can be any combination of connections and protocols that will support communications between server and client subsystems.

Subsystem 102 is shown as a block diagram with many double arrows. These double arrows (no separate reference numerals) represent a communications fabric, which provides communications between various components of subsystem 102. This communications fabric can be implemented with any architecture designed for passing data and/or control information between processors (such as microprocessors, communications and network processors, etc.), system memory, peripheral devices, and any other hardware components within a computer system. For example, the communications fabric can be implemented, at least in part, with one or more buses.

Memory 208 and persistent storage 210 are computer-readable storage media. In general, memory 208 can include any suitable volatile or non-volatile computer-readable storage media. It is further noted that, now and/or in the near future: (i) external device(s) 214 may be able to supply, some or all, memory for subsystem 102; and/or (ii) devices external to subsystem 102 may be able to provide memory for subsystem 102. Both memory 208 and persistent storage 210: (i) store data in a manner that is less transient than a signal in transit; and (ii) store data on a tangible medium (such as magnetic or optical domains). In this embodiment, memory 208 is volatile storage, while persistent storage 210 provides nonvolatile storage. The media used by persistent storage 210 may also be removable. For example, a removable hard drive may be used for persistent storage 210. Other examples include optical and magnetic disks, thumb drives, and smart cards that are inserted into a drive for transfer onto another computer-readable storage medium that is also part of persistent storage 210.

Communications unit 202 provides for communications with other data processing systems or devices external to subsystem 102. In these examples, communications unit 202 includes one or more network interface cards. Communications unit 202 may provide communications through the use of either or both physical and wireless communications links. Any software modules discussed herein may be downloaded to a persistent storage device (such as persistent storage 210) through a communications unit (such as communications unit 202).

I/O interface set 206 allows for input and output of data with other devices that may be connected locally in data communication with server computer 200. For example, I/O interface set 206 provides a connection to external device set 214. External device set 214 will typically include devices such as a keyboard, keypad, a touch screen, and/or some other suitable input device. External device set 214 can also include portable computer-readable storage media such as, for example, thumb drives, portable optical or magnetic disks, and memory cards. Software and data used to practice embodiments of the present invention, for example, program 300, can be stored on such portable computer-readable storage media. I/O interface set 206 also connects in data communication with display 212. Display 212 is a display device that provides a mechanism to display data to a user and may be, for example, a computer monitor or a smart phone display screen.

Air filter 104 is an electronic device which detects air quality metrics, such as parts per million (PPM) of a given particle or substance in the air, or an air quality index (AQI), within the surrounding area of air filter 104. For example, if it detects an airborne particle quantity above a given threshold, it may output a value indicating that there are enough irritants in the air to warrant executing safety precautions to reduce the impact of said irritants.

AR glasses 106 are an augmented reality (AR) glasses device, typically worn by an individual user in the same fashion as typical eyeglasses. Such AR glasses typically include one or more optical sensors, one or more displays, one or more electronic communication modules (such as those used to communicate information to other computers over a computer network), and one or more onboard computing components, which typically include subcomponents such as a CPU, some computer-readable storage media, and computer memory.

Ultrasonic contact lens 216 is a translucent contact lens fashioned for application to a human eyeball. This lens may include some degree of prescriptive optical correction for near-sightedness or far-sightedness. Additionally, ultrasonic contact lens 216 includes at least one piezoelectric transducer 218 (sometimes called just "transducer") that can convert physical pressure, such as that applied from a human eyelid performing a blinking or winking motion, dragging the inner surface of the eyelid across the exterior surface of a contact lens (such as 216) worn upon the underlying eyeball, into electrical energy. Piezoelectric transducer 218 (or a plurality of them, if such are present) may then store such energy into one or more electrochemical energy storage 224, which may take the form of a battery (such as lithium ion battery). Ultrasonic contact lens 216 also includes a photodiode 220, which may detect an intensity level of light present which is indicative of whether the eyelid discussed above is in an open or closed position, and also convert light into an electrical current. Antenna 222, another component of ultrasonic contact lens 216, may be used to send or receive information or commands to or from other computing devices with means of electronic communication. Computing module 223, yet another component of ultrasonic contact lens 216, includes means for processing and executing any necessary commands for the other components of ultrasonic contact lens 216 to perform their intended functionality, such as emitting ultrasonic pressure waves through piezoelectric transducer 218 using electrical energy stored in electrochemical energy storage 224 when receiving information through antenna 222 indicative of airborne eye irritants in the local area and the eyelid being open from photodiode 220.

In this embodiment, program 300 is stored in persistent storage 210 for access and/or execution by one or more computer processors of processor set 204, usually through one or more memories of memory 208. It will be understood by those of skill in the art that program 300 may be stored in a more highly distributed manner during its run time and/or when it is not running. Program 300 may include both machine readable and performable instructions and/or substantive data (that is, the type of data stored in a database). In this particular embodiment, persistent storage 210 includes a magnetic hard disk drive. To name some possible variations, persistent storage 210 may include a solid state hard drive, a semiconductor storage device, read-only memory (ROM), erasable programmable read-only memory (EPROM), flash memory, or any other computer-readable storage media that is capable of storing program instructions or digital information.

The programs described herein are identified based upon the application for which they are implemented in a specific embodiment of the invention. However, it should be appreciated that any particular program nomenclature herein is used merely for convenience, and thus the invention should not be limited to use solely in any specific application identified and/or implied by such nomenclature.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

II. Example Embodiment

Figure 2:
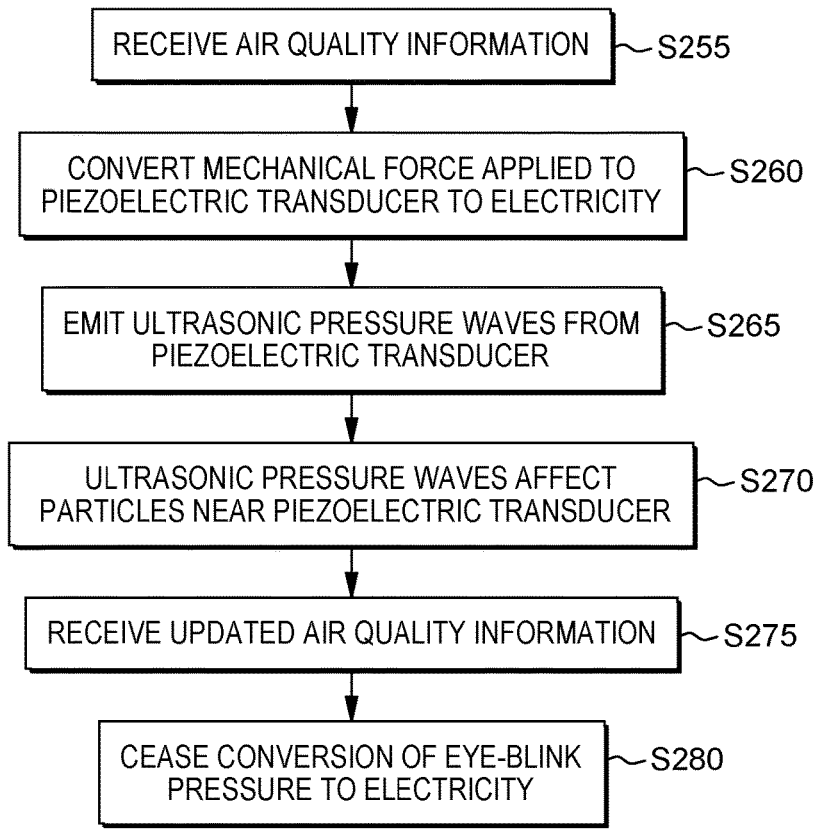
FIG. 2 is a flowchart showing a first embodiment method performed, at least in part, by the first embodiment system.
Figure 3:
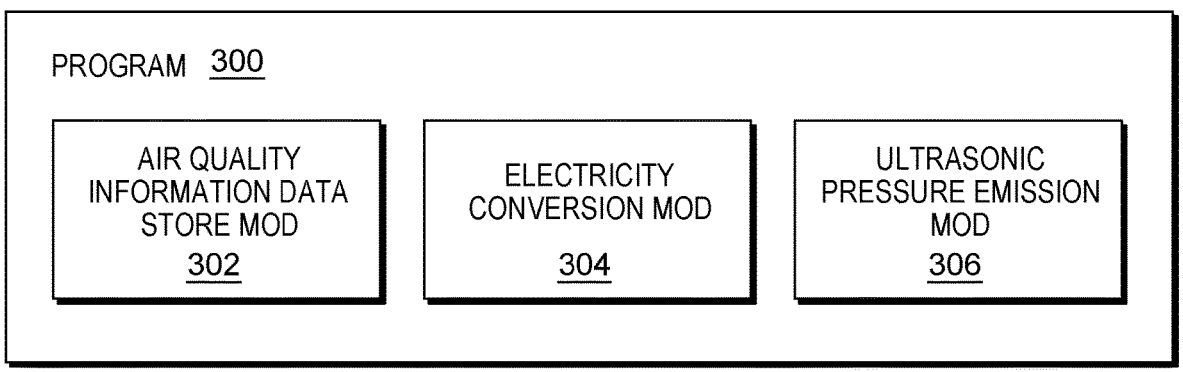
FIG. 3 is a block diagram showing a machine logic (for example, software) portion of the first embodiment system.

As shown in FIG. 1, networked computers system 100 is an environment in which an example method according to the present invention can be performed. As shown in FIG. 2, flowchart 250 shows an example method according to the present invention. As shown in FIG. 3, program 300 performs or control performance of at least some of the method operations of flowchart 250. This method and associated software will now be discussed, over the course of the following paragraphs, with extensive reference to the blocks of FIGS. 1, 2 and 3, as well as the diagrams of FIGS. 4A, 4B, 4C and 5.

Figure 4A:
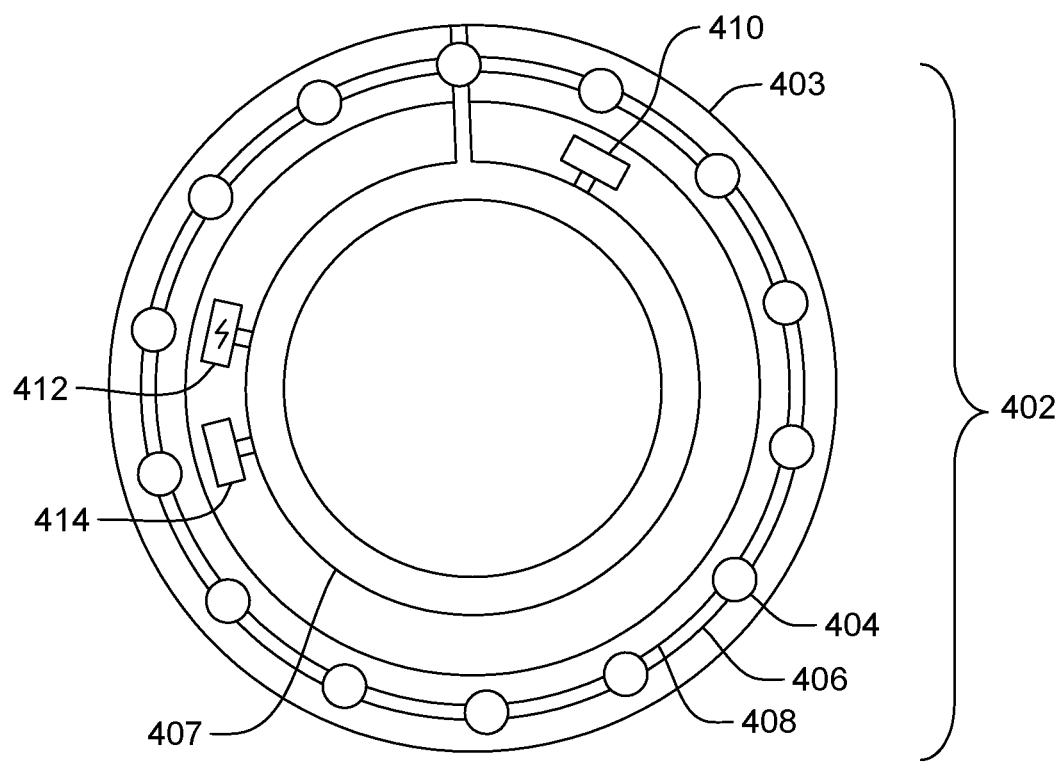
FIG. 4A is a top-down perspective view of an ultrasonic contact lens of the first embodiment system.
Figure 4B:
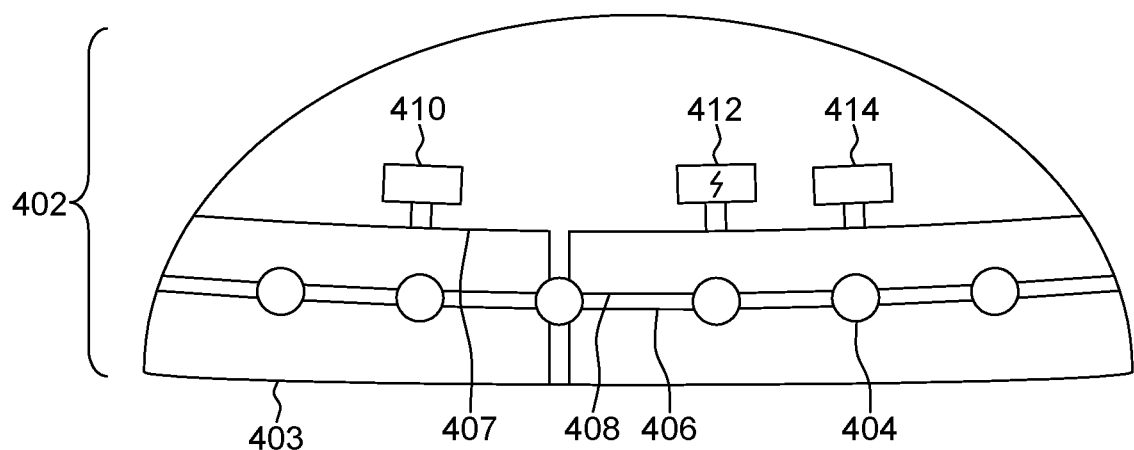
FIG. 4B is a side perspective view of an ultrasonic contact lens of the first embodiment system.
Figure 4C:
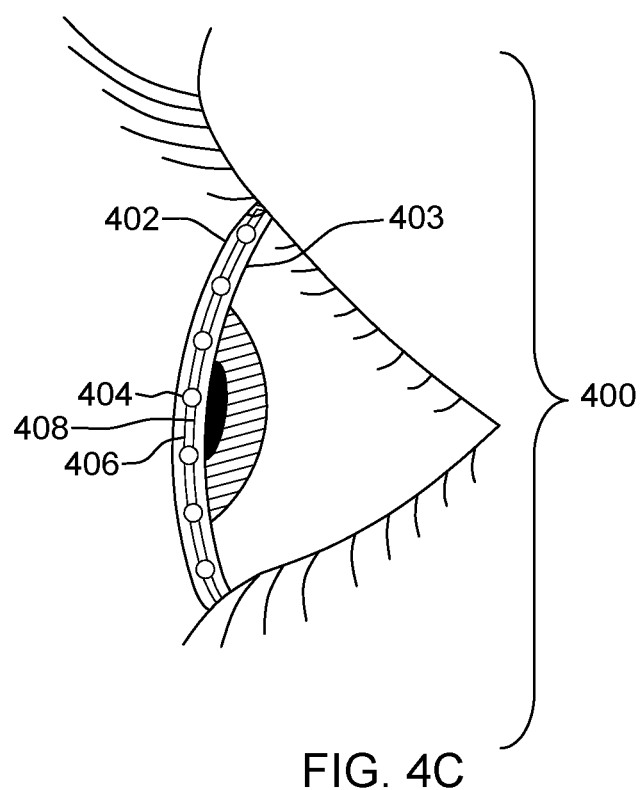
FIG. 4C is a side perspective view of an eye equipped with an ultrasonic contact lens of the first embodiment system.
Figure 5:
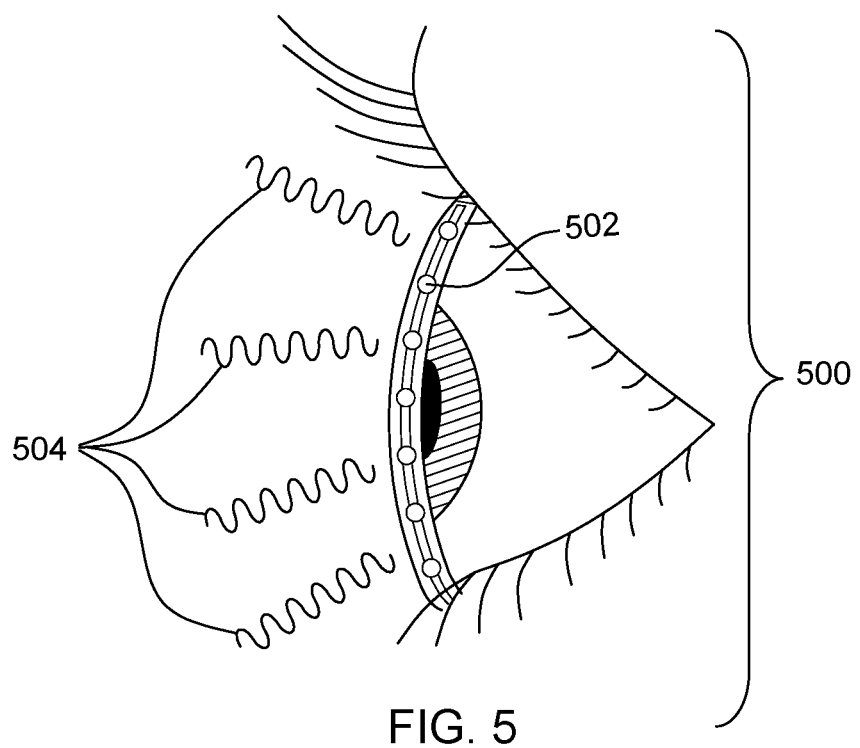
FIG. 5 is a side perspective view of an eye equipped with an ultrasonic contact lens emitting ultrasonic pressure waves of the first embodiment system.

Processing begins at operation S255, where air quality information data store module ("mod") 302 receives from air filter 104 of FIG. 1 through network 114 information indicative of the presence of airborne eye irritants in the proximity of a user ("the user") wearing ultrasonic contact lens 216 ("the lens"). In this simplified embodiment, the user is wearing ultrasonic contact lens 216 on at least one of their eyeballs ("the eyeball"), as shown in FIG. 4C. FIG. 4C includes a diagram of human eye 400 which includes the eyeball, wearing ultrasonic contact lens 402 (shown as 216 in FIG. 1), antenna 403 (shown as 222 in FIG. 1), piezoelectric transducer 404 (shown as 218 in FIG. 1), and electrical connections 406 and 408 running among and between the components of the lens, further shown in FIGS. 4A and 4B. FIGS. 4A and 4B respectively show top-down and side-view perspective diagrams of the lens shown in diagram 400 of FIG. 4C. As shown in FIGS. 4A and 4B, piezoelectric transducer 404 are arranged along the convex surface of the lens 402 proximate to antenna 403, which is itself placed along the outer circumference of the lens, which are all connected through connections 406 and 408. Connections 406 and 408 are further connected to an inner connection 407, which connects to electrochemical energy storage 412 (shown as 224 in FIG. 1), photodiode 414 (shown as 220 in FIG. 1), and computing module 410 (shown as 223 in FIG. 1). Antenna 403 is strategically placed to improve the capabilities of an antenna incorporated into such a device as the lens, as the range of an antenna is affected by the length of the material provided for use as an antenna, and the outer circumference of the lens represents a greater length than another single circumference within the lens, such as that shown in inner connection 407. Alternatively, the user would wear an ultrasonic contact lens on each of their eyeballs to prevent or mitigate irritation from airborne particles.

Information indicative of the presence of airborne eye irritants in the context of this simplified embodiment is the presence of mold spores measured in parts per-million ("PPM") above a predefined threshold, which is 500 PPM in this simplified embodiment. In alternative embodiments, other predefined thresholds may be used, or dynamically set thresholds such as deviating above a threshold by a predefined percentage, where the threshold is determined based upon a moving average over a predefined period of time. For example, if the mold spores in PPM jumped by more than 10% above the average over the last 7 days, the threshold would be determined to be exceeded. In this simplified embodiment, the amount of mold spores in PPM indicated in the received information is 750 PPM, well above the 500 PPM threshold indicated above. In alternative embodiments, other types of airborne eye irritants may be used. For example, bacteria, viruses, dust, debris, etc.

Processing proceeds to operation S260 of FIG. 2, where electricity conversion mod 304 instructs ultrasonic contact lens 216 of FIG. 1 to begin converting mechanical force applied to piezoelectric transducer 218 into electricity or electrical energy. In this simplified embodiment, the instruction from program 300 is transmitted from smartphone sub-system 102 of FIG. 1 through wireless electronic communication that is received by antenna 222. In this simplified embodiment, the mechanical force applied to the piezoelectric transducer is supplied by force exerted by the eyelid of the eyeball as it conducts a blinking or winking motion. That is, as the eyelid slides along the convex surface of the lens and transducer 218, it applied mechanical force upon transducer 218, which in turn is converted into electrical energy. Also in this simplified embodiment, this electricity is used locally to emit ultrasonic pressure waves through the same transducer that converted the electricity, and stored in electrochemical energy storage 224 if there is no present demand for the electrical energy, such as when photodiode 220 indicates that the eye is closed and therefore presently protected from airborne irritants. Photodiode 220 is also used to generate electricity when the eye is open, ensuring that there is a relatively continuous supply of energy converted into electricity for the contact lens to use to emit ultrasonic pressure waves or for other uses.

Processing proceeds to operation S265, where piezoelectric transducer 218 of FIG. 1 emits ultrasonic pressure waves. In this simplified embodiment, piezoelectric transducer emits ultrasonic pressure waves, or waves of air pressure at ultrasonic frequencies, as shown in lens equipped eye diagram 500 of FIG. 5, where piezoelectric transducer 502 (also shown as piezoelectric transducer 404 in FIGS. 4A and 4B and piezoelectric transducer 218 in FIG. 1) emits ultrasonic pressure waves 504 into the surrounding environment. In this simplified embodiment, the piezoelectric transducer does not emit ultrasonic pressure waves unless photodiode 220 of FIG. 1 indicates that the eyelid is in a partially or completely open position (as opposed to a fully closed position). Electricity for generating the ultrasonic pressure waves by transducer 218 is supplied from blinking and winking motions of the eyelid as described in S260. As the user continues to blink and/or wink the eyelid of the eye equipped with the lens, the transducer 218 generates electricity, which is then either stored in electrochemical storage 224 or used to generate ultrasonic pressure waves by transducer 218.

Processing proceeds to operation S270, where the ultrasonic pressure waves emitted at S265 affect airborne particles near piezoelectric transducer 218 where such particles are also in close proximity to the eye of the user. In this simplified embodiment, the ultrasonic pressure waves emitted from piezoelectric transducer 218 of FIG. 1 affect airborne particles which are closely proximate to the users eyeball (and therefore, transducer 218 of FIG. 1 and ultrasonic contact lens 216) by destroying airborne microorganisms, including the mold spores which were measured at 500 PPM. As airborne microorganisms travel closer to the source of the ultrasonic pressure waves (transducer 218), they are subjected to ultrasonic waves of increasing intensity. As the lens effectively obstructs direct contact with a significant portion of the eyeball, the eyeball is effectively sheathed with a field of ultrasonic pressure waves that must be traversed (with increasing intensity) in order for airborne particles such as airborne microorganisms to reach the surface of the eye and begin infection and irritation.

Processing proceeds to operation S275, where air quality information data store mod 302 receives from air filter 104 of FIG. 1 through network 114 updated air quality information indicative of a "safe" level of airborne eye irritants in the proximity of the wearing ultrasonic contact lens 216. In this simplified embodiment, the "safe" level of airborne eye irritants is a reduction of mold spores below the threshold of 500 PPM. In this simplified embodiment, the updated air quality information indicates a measurement of mold spores of 10 PPM, well below the above indicated threshold. This updated information indicates that ultrasonic pressure waves are no longer required to protect the eye from airborne irritants, such as the mold spores. In this simplified embodiment, smartphone sub-system 102 receives the updated air quality information from air filter 104 through network 114.

Processing proceeds to operation S280, where electricity conversion mod 304 instructs ultrasonic contact lens 216 of FIG. 1 to cease conversion of eye-blink pressure into electricity. In this simplified embodiment, responsive to receiving the updated air quality information at S275, program 300 transmits an instruction to ultrasonic contact lens 216 via wireless electronic communication, which is received through antenna 222 and processed through computing module 223, instructing the lens to deactivate piezoelectric transducer 218 from converting mechanical energy from eye-blinks and winks into electrical energy and to cease emitting ultrasonic pressure waves.

In an alternative embodiment, AR glasses 106 are used in substitute for smartphone sub-system 102. In this alternative embodiment, AR glasses 106 includes substantially the same components of smartphone sub-system 102, with similar processing and communication abilities of a smartphone, but designed into a compact form-factor to be worn as a pair of eyeglasses. These AR glasses have the advantage over a typical smartphone of being positioned closer to the ultrasonic contact lenses worn by an individual also wearing the AR glasses as the AR glasses would typically be much more closer in proximity during typical usage than a typical smartphone, reducing the required strength of the antenna incorporated into the ultrasonic contact lenses for communication purposes, such as antenna 222. As a further alternative, AR glasses 106 may be used in conjunction with smartphone sub-system 102 to serve as a sort of communication relay between smartphone sub-system 102 and ultrasonic contact lens 216 by passing information between the two other devices. AR glasses 106 have a form factor that would allow for more robust wireless electronic communication over that which may be embedded within a contact lens.

In an alternative embodiment, if the air quality information indicates information indicative that airborne irritants in the air exceeds a second, higher threshold, program 300 communicates a notification to the user through smartphone sub-system 102 that the air quality is too contaminated for mitigation by ultrasonic contact lens 216 alone, and that more robust eye protection measures are to be deployed to prevent eye irritation from airborne particles. For example, if a first threshold is mold spores of 500 PPM, then a second threshold might be 2500 PPM. Referring to an earlier alternative embodiment for dynamically adjusting the threshold for activating the piezoelectric transducer, the second threshold may be a further percentage increase over the time period, such as a 500% increase in PPM over the average of the last 7 days.

III. Further Comments and/or Embodiments

Some embodiments of the present invention recognize the following facts, potential problems and/or potential areas for improvement with respect to the current state of the art: (i) there are many contagious diseases and infections (bacterial, viral and fungal) which affect the eyes; (ii) these diseases are transmitted when a person's eye is exposed to polluted surroundings through the air, water, dust and exposure to an already infected person; (iii) floating micro dust particles can also enter the eyes and cause irritation; and (iv) what is needed is a way to overcome this problem by creating a layer which can protect the user from eye-based infection transmissions.

Some embodiments of the present invention may include one, or more, of the following operations, features, characteristics and/or advantages: (i) disclosed is a method and system by which smart contact lens will be emitting controlled ultrasound when user opens his eyes; (ii) the ultrasound will kill infection causing organisms (like bacteria) near the eyes of the user thereby protecting the user from eye infections and infections transmitted through the eye; (iii) disclosed system and method is extensible to AR glasses/devices; (iv) a device for non-invasive treatment of bacterial growth; (v) the extension device can keep monitoring (for example, keep taking high-res pictures) the eye and send data to a smart phone for analysis; (vi) the smart phone can then identify whether the pre-existing bacterial growth has increased or decreased and then emit ultrasonic waves into specific parts of the eye as therapy); (vii) though it is possible to instead use antibiotics, occasionally a patient might be allergic to such substances, in which case this technique will be helpful; (viii) emit ultrasound using an array of piezoelectric transducer chips installed along the circumference of smart contact lenses to kill and/or reduce the impact of bacterial, viral and fungal infections that transmit via the eyes; (ix) track when the user will open and close their eyes to activate the piezoelectric transducer chip to emit the ultrasound and kill and/or reduce the impact of infections; (x) as an alternative embodiment, the smart contact lenses interact with the IoT ecosystem in the surrounding area to identify the areas where risks of infections may be heightened to operate the ultrasonic smart contact lenses to kill and/or reduce the impact of infections; (xi) the smart contact lenses will interact with any air purifier(s) or any other device that decontaminates the air or measures the air quality in the surrounding area; and (xii) if the air quality is good, the contact lens will not trigger the piezoelectric transducer chips thereby not emitting the ultrasound wave.

Figure 6:
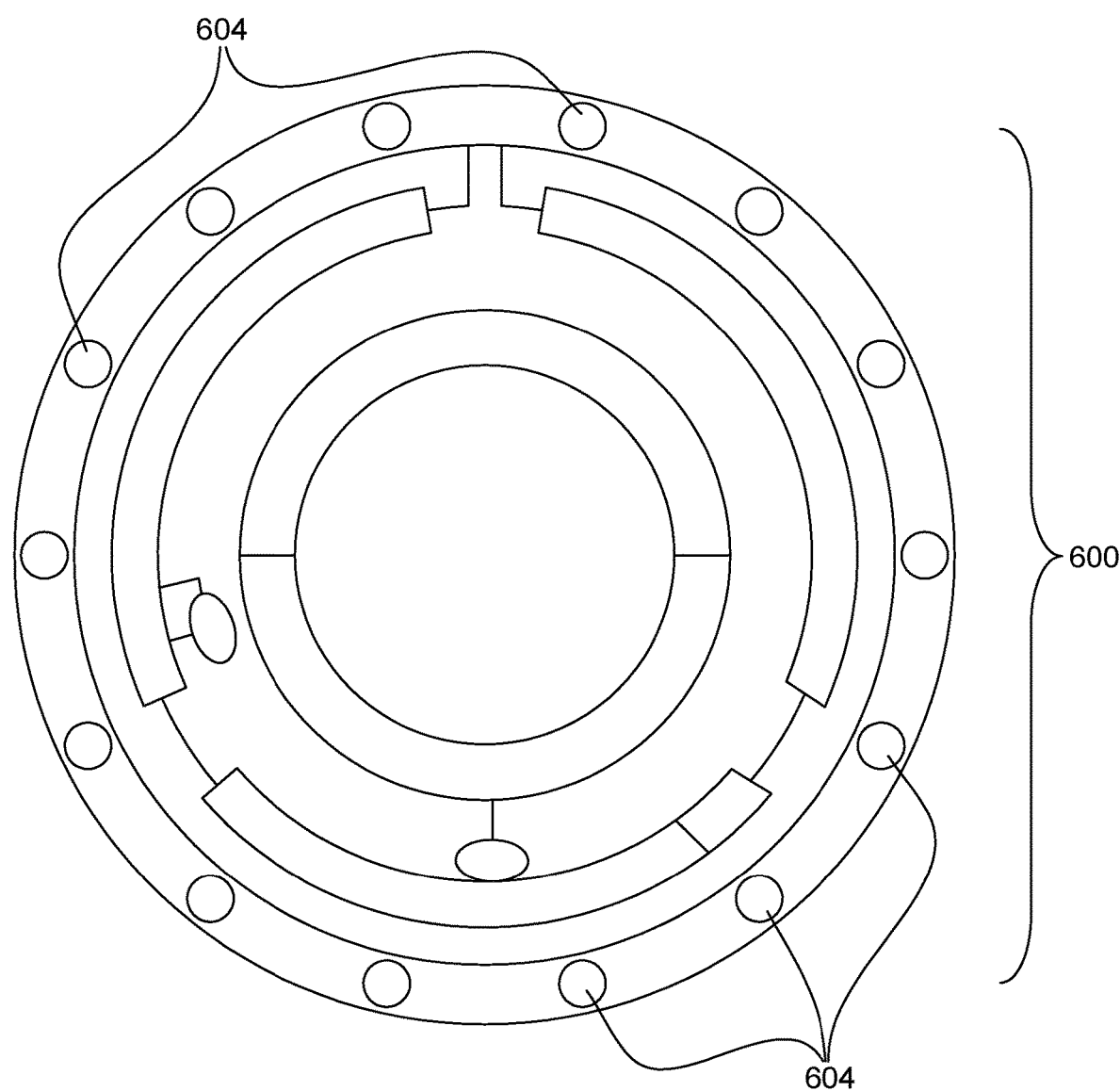
FIG. 6 is a top-down perspective view of an ultrasonic contact lens of a second embodiment system.

Following diagram 600 of FIG. 6 illustrates a smart contact lens having an array of Piezoelectric transducers 604 around the circumference. The smart contact lens emits ultrasonic vibrations directed outwards from an eye wearing the lens when conditions are present suggesting a likelihood of contracting an eye infection is identified in the surrounding area.

Some embodiments of the present invention may include one, or more, of the following operations, features, characteristics and/or advantages: (i) as per the proposed system, Piezoelectric chips are embedded within a pair of smart contact lenses; (ii) blinking of the user's eyes will power each contact lens using piezoelectric sensors that convert the eye movement into electric power; (iii) as per invention, opposite method (inversion) will be used, where electricity previously generated by the Piezoelectric chips will be applied in Piezoelectric chips to create mechanical force; (iv) the array of Piezoelectric transducer chips will be fixed along the circumference of smart contact lens; (v) these chips will generate ultrasound waves; (vi) the smart contact lenses can be paired with a user's mobile device or any other wearable devices; (vii) for paring, any technology which is safe for eyes can be used; (viii) the user's devices will communicate with IoT devices and sensors available in the surrounding area to identify the contextual surrounding and user's relative position in the surrounding; (ix) the contextual surrounding can be a hospital, a disaster area, etc.; (x) based on the contextual surrounding and analyzed information, the IoT enabled system predict that the surroundings risk exposure to contaminated air with a probability of the user's eyes getting infected; (xi) the proposed system will also be tracking if the user is in a surrounding (which may or may not be enclosed), where an air purifier is installed or any other mechanism is installed which is destroys germs or contaminants; (xii) the smart contact lens will communicate with devices in the surrounding area to identify if there is contaminated air that may infect the eye; (xiii) the smart contact lens includes a photodiode and, accordingly, based on the photodiode feed, the smart contact lens will recognize the user blinking their eye; (xiv) based on the user's blinking pattern and predicted presence of infection in the area near the eye, the Piezoelectric transducer chips will be triggered by the smart contact lens to generate and emit ultrasound; (xiv) the direction of ultrasound generation will be outwards from the eye opening; (xv) the ultrasound emitted will destroy microorganisms that can cause infection close to the user's eye; (xvi) if the surrounding ecosystem identifies there is no risks relating to floating infections, then the Piezoelectric transducer will be stopped, and ultrasound will not be generated; (xvii) the smart contact lens includes a continuous power supply mechanism, where the photo electric diode generates power when visible light falls on the eye (the eye is open); and (xviii) the generated power will supply the Piezoelectric transducer the power to generate ultrasound wave.

Some embodiments of the present invention may include one, or more, of the following operations, features, characteristics and/or advantages: (i) kill and/or reduce the impact of bacterial, viral and fungal infections as a means to protect an uninfected eye; (ii) the approach in some embodiments is proactive rather than reactive; (iii) this is achieved by using a Piezoelectric transducer chip in a smart contact lens to emit ultrasound; (iv) further, the smart contact lens can pair with the IoT ecosystem in the surrounding area to assess the air-quality and potential existence of bacteria, virus and fungus; (v) a system and method to protect a user's eye from getting infected due to bacterial, viral and fungal infections in the area surrounding the eyes; (vi) to achieve this, an array of Piezoelectric transducer chips installed along the circumference of smart contact lenses will emit ultrasound waves to kill and/or reduce the impact of infections; (vii) the Piezoelectric transducer chips emit ultrasound when the user opens or closes the eyes; (viii) the smart contact lenses can interact with the IoT ecosystem in the surrounding area to assess air-quality and potential existence of bacterial, viral or fungal infections; (ix) if the air quality is good, the contact lens will not trigger the Piezoelectric transducer chips thereby not emitting he ultrasonic waves; (x) interaction of the smart contact lenses with the internet of things (IoT) ecosystem in the surrounding area to identify the areas where the smart contact lenses requires to operate to kill and/or reduce the impact of infections; (xi) further interacting of the smart contact lenses with any air purifiers or any other device that de-contaminates the air or measures the air quality in the surrounding area; (xii) the smart contact lenses are placed on the user's eyes; (xiii) at least two piezoelectric transducers are used to provide coverage of the volume of area near the eye approximately equal to the thickness and surface of the eyelids.

An embodiment of the present invention includes a system and/or method that emits ultrasound using an array of Piezoelectric transducer chip installed along the circumference of smart contact lenses to kill and/or reduce the impact of bacterial, viral and fungal infections that transmit via the eyes.

An alternative embodiment of the present invention includes: (i) a system and/or method that emits ultrasound using an array of Piezoelectric transducer chip installed along the circumference of smart contact lenses to kill and/or reduce the impact of bacterial, viral and fungal infections that transmit via the eyes; and (ii) the system/method will track when the user will open and close their eyes to activate the Piezoelectric transducer chip to emit the ultrasound and kill and/or reduce the impact of infections.

A further alternative embodiment of the present invention includes: (i) a system and/or method that emits ultrasound using an array of Piezoelectric transducer chip installed along the circumference of smart contact lenses to kill and/or reduce the impact of bacterial, viral and fungal infections that transmit via the eyes; (ii) the system/method will track when the user will open and close their eyes to activate the Piezoelectric transducer chip to emit the ultrasound and kill and/or reduce the impact of infections; and (iii) the smart contact lenses interact with the IoT ecosystem in the surrounding area to identify the areas where the smart contact lenses will require to operate to kill and/or reduce the impact of infections.

A yet further alternative embodiment of the present invention includes: (i) a system and/or method that emits ultrasound using an array of Piezoelectric transducer chip installed along the circumference of smart contact lenses to kill and/or reduce the impact of bacterial, viral and fungal infections that transmit via the eyes; (ii) the system/method will track when the user will open and close their eyes to activate the Piezoelectric transducer chip to emit the ultrasound and kill and/or reduce the impact of infections; and (iii) the smart contact lenses interact with the IoT ecosystem in the surrounding area to identify the areas where the smart contact lenses will require to operate to kill and/or reduce the impact of infections; (iv) the smart contact lenses will interact with any air purifier(s) or any other device that de-contaminates the air or measures the air quality in the surrounding area; and (v) if the air quality is good, the contact lens will not trigger the Piezoelectric transducer chips thereby not emitting the ultrasound wave.

IV. Definitions

Present invention: should not be taken as an absolute indication that the subject matter described by the term "present invention" is covered by either the claims as they are filed, or by the claims that may eventually issue after patent prosecution; while the term "present invention" is used to help the reader to get a general feel for which disclosures herein are believed to potentially be new, this understanding, as indicated by use of the term "present invention," is tentative and provisional and subject to change over the course of patent prosecution as relevant information is developed and as the claims are potentially amended.

Embodiment: see definition of "present invention" above—similar cautions apply to the term "embodiment."

and/or: inclusive or; for example, A, B "and/or" C means that at least one of A or B or C is true and applicable.

In an Including/include/includes: unless otherwise explicitly noted, means "including but not necessarily limited to."

Module/Sub-Module: any set of hardware, firmware and/or software that operatively works to do some kind of function, without regard to whether the module is: (i) in a single local proximity; (ii) distributed over a wide area; (iii) in a single proximity within a larger piece of software code; (iv) located within a single piece of software code; (v) located in a single storage device, memory or medium; (vi) mechanically connected; (vii) electrically connected; and/or (viii) connected in data communication.

Computer: any device with significant data processing and/or machine readable instruction reading capabilities including, but not limited to: desktop computers, mainframe computers, laptop computers, field-programmable gate array (FPGA) based devices, smart phones, personal digital assistants (PDAs), body-mounted or inserted computers, embedded device style computers, and application-specific integrated circuit (ASIC) based devices.

Electrically Connected: means either directly electrically connected, or indirectly electrically connected, such that intervening elements are present; an electrical connection may include, but need not be limited to, elements such as capacitors, inductors, transformers, vacuum tubes, and the like.

Data communication: any sort of data communication scheme now known or to be developed in the future, including wireless communication, wired communication and communication routes that have wireless and wired portions; data communication is not necessarily limited to: (i) direct data communication; (ii) indirect data communication; and/or (iii) data communication where the format, packetization status, medium, encryption status and/or protocol remains constant over the entire course of the data communication.

What is claimed is:

1. An ultrasonic emitting electronic contact lens apparatus placed on an eyeball comprising:
    a translucent lens portion having a concave surface and a convex surface; and
    a plurality of piezoelectric transducer portions embedded upon the convex surface, where the plurality of piezoelectric transducer portions are arranged along the outer circumference of the convex surface, and the plurality of piezoelectric transducer portions emit ultrasonic pressure waves, wherein the plurality of piezoelectric transducer portions emit ultrasonic pressure waves away from the eyeball and are configured to remove one or more microparticles from air in front of the contact lens.

2. The ultrasonic emitting electronic contact lens apparatus of claim 1, further comprising:
    an antenna portion affixed along the edge of the outer circumference of the translucent lens portion, the antenna portion electrically connected to the plurality of piezoelectric transducer portions.

3. The ultrasonic emitting electronic contact lens apparatus of claim 2, further comprising:
    a photodiode portion affixed between the outer circumference of the translucent lens portion and the center of the translucent lens portion, with the photodiode electrically connected to the plurality of piezoelectric transducer portions and the photodiode converts electromagnetic light photons into electrical energy.

4. The ultrasonic emitting electronic contact lens apparatus of claim 3, further comprising:
    a computing module portion affixed between the outer circumference of the translucent lens portion and the center of the translucent lens portion, with the computing module portion electrically connected to the plurality of piezoelectric transducer portions, the antenna and the photodiode, and the computing module including a computer processor and memory.

5. The ultrasonic emitting electronic contact lens apparatus of claim 4, further comprising:
    an electrochemical energy storage portion affixed to the translucent lens and electrically connected to the plurality of piezoelectric transducer portions, the photodiode portion, the antenna portion, and the computing module portion.

6. The ultrasonic emitting electronic contact lens apparatus of claim 5, wherein the antenna portion communicated with an augmented reality (AR) glasses device through wireless electronic communication.

7. A computer-implemented method (CIM) for use with a contact lens placed on an eyeball, with the contact lens including a plurality of piezoelectric transducers, the CIM comprising:
    responsive to a blinking motion of an eyelid over the eyeball, converting pressure from the blinking motion of the eyelid applied to the piezoelectric transducers into electrical energy;
    emitting, using the converted electrical energy, ultrasonic pressure waves through the piezoelectric transducers; and
    removing one or more microparticles from air in front of the contact lens using the ultrasonic pressure waves emitted through the piezoelectric transducers away from the eyeball.

8. The CIM of claim 7, further comprising:
    detecting, through a photodiode, an increased presence of light indicative of an eyelid of the eyeball being in an at least partially opened state;
    wherein emitting ultrasonic pressure waves is responsive to detecting the increased presence of light.

9. The CIM of claim 8, further comprising:
responsive to detecting the increased presence of light, converting at least some of that light into electrical energy.

10. The CIM of claim 9, further comprising:
storing at least some of the electrical energy converted by the photodiode into an electrochemical energy storage module; and
storing at least some of the electrical energy converted by the plurality of piezoelectric transducers into an electrochemical energy storage module.

11. The CIM of claim 7, further comprising:
receiving an air quality data set including information indicative of presence of airborne eye irritants in proximity to a user wearing the contact lens exceeding a predefined threshold;
wherein the converting of pressure from blinking motion of the eyelid applied to the piezoelectric transducers into electrical energy is further responsive to the received air quality data set including information indicative of the presence of airborne eye irritants in proximity to the user wearing the contact lens exceeding the predefined threshold.

12. The CIM of claim 7, further comprising:
receiving an air quality data set including information indicative of presence of airborne eye irritants in proximity to a user wearing the contact lens falling below a predefined threshold;
responsive to the received air quality data set including information indicative of presence of airborne eye irritants in proximity to the user wearing the contact lens falling below a predefined threshold, ceasing the emission of ultrasonic pressure waves through the piezoelectric transducers.

13. A computer system (CS) for use with a contact lens placed on an eyeball, with the contact lens including a plurality of piezoelectric transducers, the CS comprising:
a processor(s) set;
a contact lens placed on the eyeball, the contact lens having a plurality of piezoelectric transducers;
a set of storage device(s); and
computer code stored collectively in the set of storage device(s), with the computer code including data and instructions to cause the processor(s) set to perform at least the following operations:
responsive to a blinking motion of an eyelid over the eyeball, converting pressure from the blinking motion of the eyelid applied to the piezoelectric transducers into electrical energy;
emitting, using the converted electrical energy, ultrasonic pressure waves through the piezoelectric transducers; and
removing one or more microparticles from air in front of the contact lens using the ultrasonic pressure waves emitted through the piezoelectric transducers away from the eyeball.

14. The CS of claim 13, wherein the computer code further includes instructions for causing the processor(s) set to perform the following operations:
detecting, through a photodiode, an increased presence of light indicative of an eyelid of the eyeball being in an at least partially opened state;
wherein emitting ultrasonic pressure waves is responsive to detecting the increased presence of light.

15. The CS of claim 14, wherein the computer code further includes instructions for causing the processor(s) set to perform the following operations:
responsive to detecting the increased presence of light, converting at least some of that light into electrical energy.

16. The CS of claim 15, wherein the computer code further includes instructions for causing the processor(s) set to perform the following operations:
storing at least some of the electrical energy converted by the photodiode into an electrochemical energy storage module; and
storing at least some of the electrical energy converted by the plurality of piezoelectric transducers into an electrochemical energy storage module.

17. The CS of claim 13, wherein the computer code further includes instructions for causing the processor(s) set to perform the following operations:
receiving an air quality data set including information indicative of presence of airborne eye irritants in proximity to a user wearing the contact lens exceeding a predefined threshold;
wherein the converting of pressure from blinking motion of the eyelid applied to the piezoelectric transducers into electrical energy is further responsive to the received air quality data set including information indicative of the presence of airborne eye irritants in proximity to the user wearing the contact lens exceeding the predefined threshold.

18. The CS of claim 13, wherein the computer code further includes instructions for causing the processor(s) set to perform the following operations:
receiving an air quality data set including information indicative of presence of airborne eye irritants in proximity to a user wearing the contact lens falling below a predefined threshold;
responsive to the received air quality data set including information indicative of presence of airborne eye irritants in proximity to the user wearing the contact lens falling below a predefined threshold, ceasing the emission of ultrasonic pressure waves through the piezoelectric transducers.

\* \* \* \* \*